US010799170B1

(12) United States Patent
Schindler et al.

(10) Patent No.: US 10,799,170 B1
(45) Date of Patent: Oct. 13, 2020

(54) APPARATUS FOR MEASURING ISOMETRIC MUSCLE STRENGTH

(71) Applicant: U.S. Government as Represented by the Secretary of the Army, Natick, MA (US)

(72) Inventors: Jessica B. Schindler, Wayland, MA (US); Stephen C. MacIntosh, Billerica, MA (US); James J McLaughlin, North Attleboro, MA (US)

(73) Assignee: U.S. Government as Represented by the Secretary of the Army, Washington, DC (US)

( * ) Notice: Subject to any disclaimer, the term of this patent is extended or adjusted under 35 U.S.C. 154(b) by 107 days.

(21) Appl. No.: 16/272,151

(22) Filed: Feb. 11, 2019

(51) Int. Cl.
| | |
|---|---|
| *A61B 5/103* | (2006.01) |
| *A61B 5/117* | (2016.01) |
| *A61B 17/60* | (2006.01) |
| *A61B 5/22* | (2006.01) |
| *A63B 21/002* | (2006.01) |

(52) U.S. Cl.
CPC ............ *A61B 5/224* (2013.01); *A63B 21/002* (2013.01); *A63B 2220/51* (2013.01)

(58) Field of Classification Search
CPC ......... A61B 5/103; A61B 5/117; A61B 17/60; G01L 5/02
See application file for complete search history.

(56) References Cited

U.S. PATENT DOCUMENTS

| | | |
|---|---|---|
| 2,855,199 A | 10/1958 | Noland |
| 3,285,070 A | 11/1966 | McDonough |
| 3,374,675 A | 3/1968 | Keropian |
| 3,752,144 A | 8/1973 | Weigle |
| 4,333,340 A | 6/1982 | Elmeskog |
| 4,462,252 A | 7/1984 | Smidt |

(Continued)

FOREIGN PATENT DOCUMENTS

| | | |
|---|---|---|
| CN | 201691940 U | 1/2011 |
| CN | 201759570 U | 3/2011 |
| DE | 202015001800 U1 | 4/2015 |

OTHER PUBLICATIONS

Bohannon, R. W. (1986). Test-retest reliability of hand-held dynamometry during a single session of strength assessment. Physical therapy, 66(2), 206-209.

(Continued)

*Primary Examiner* — Jewel V Dowtin
(74) *Attorney, Agent, or Firm* — Roger C. Phillips

(57) ABSTRACT

An apparatus to measure isometric muscle strength has a table section having a top surface adapted to allow a person to sit thereon. An upright frame section is movably attached to the table section and spans the top surface and includes an open area sized to allow the person's legs and thighs to extend therethrough when the person is seated on the top surface. A cradle is attached to the frame section and holds a force-measuring device that is acted upon by the person's body segment when the person is seated on the top surface. Movement-impeding devices allow or prevent movement of the frame section. Belts and/or straps are attached to the table section and adapted to be secured to various parts of the person's body to stabilize the person on the top surface and to isolate muscle groups that are to be tested for isometric muscle strength.

20 Claims, 13 Drawing Sheets

(56) References Cited

U.S. PATENT DOCUMENTS

| | | | |
|---|---|---|---|
| 4,493,485 A | | 1/1985 | Jones |
| 4,501,148 A | | 2/1985 | Nicholas |
| D283,987 S | | 5/1986 | Smidt |
| 4,702,108 A | | 10/1987 | Amundsen |
| 4,725,056 A | | 2/1988 | Rehrl |
| 4,823,807 A | * | 4/1989 | Russell ............... A61B 5/1121 600/586 |
| 5,090,421 A | | 2/1992 | Wagoner, III |
| 5,335,674 A | * | 8/1994 | Siegler ................. A61B 5/103 600/592 |
| 5,662,591 A | | 9/1997 | Peindl |
| 6,227,047 B1 | | 5/2001 | Livingston |
| 6,325,767 B1 | | 12/2001 | Wolff |
| 6,551,258 B1 | * | 4/2003 | Herling ................. A61B 5/103 600/595 |
| 6,595,904 B1 | | 7/2003 | Staffa |
| 6,773,376 B2 | | 8/2004 | Dvir |
| 7,753,862 B2 | * | 7/2010 | Branch ............... A61B 5/4533 601/5 |
| 8,216,157 B2 | * | 7/2012 | Leunig ................. A61B 5/1071 600/587 |
| 9,566,022 B2 | * | 2/2017 | Imhauser ............ A61B 5/1124 |
| 9,603,768 B1 | * | 3/2017 | Widmer ................. A61H 1/024 |
| 10,667,746 B2 | * | 6/2020 | Imhauser ............ A61B 5/6835 |
| 2008/0216570 A1 | | 9/2008 | Andres |

OTHER PUBLICATIONS

Wikholm, J. B., & Bohannon, R. W. (1991). Hand-held dynamometer measurements: tester strength makes a difference. Journal of Orthopaedic & Sports Physical Therapy, 13(4), 191-198.

Andrews, A. W., Thomas, M. W., & Bohannon, R. W. (1996). Normative values for isometric muscle force measurements obtained with hand-held dynamometers. Physical therapy, 76(3), 248-259.

Bohannon, R. W. (1999). Intertester reliability of hand-held dynamometry: a concise summary of published research. Perceptual and Motor Skills, 88(3), 899-902.

Bandinelli, S., Benvenuti, E, Del Lungo, I., Baccini, M., Benvenuti, F., Di Iorio, A., & Ferrucci, L. (1999). Measuring muscular strength of the lower limbs by hand-held dynamometer: a standard protocol. Aging Clinical and Experimental Research, 11(5), 287-293.

Nadler, S. F., DePrince, M. L., Hauesien, N., Malanga, G. A., Stitik, T. P., & Price, E. (2000). Portable dynamometer anchoring station for measuring strength of the hip extensors and abductors. Archives of physical medicine and rehabilitation, 81(8), 1072-1076.

Scott, D. A., Bond, E Q., Sisto, S. A., & Nadler, S. F. (2004). The intra-and interrater reliability of hip muscle strength assessments using a handheld versus a portable dynamometer anchoring station 1. Archives of physical medicine and rehabilitation, 85(4), 598-603.

Kelln, B. M., McKeon, P. O., Gontkof, L. M., & Hertel, J. (2008). Hand-held dynamometry: reliability of lower extremity muscle testing in healthy, physically active, young adults. Journal of sport rehabilitation, 17(2), 160-170.

Katoh, M., & Yamasaki, H. (2009). Test-retest reliability of isometric leg muscle strength measurements made using a hand-held dynamometer restrained by a belt: comparisons during and between sessions. Journal of Physical Therapy Science, 21(3), 239-243.

Katoh, M., & Yamasaki, H. (2009). Comparison of reliability of isometric leg muscle strength measurements made using a hand-held dynamometer with and without a restraining belt. Journal of physical therapy science, 21(1), 37-42.

Gordon, C. C., Blackwell, C. L., Bradtmiller, B., Parham, J. L., Barrientos, P., Paquette, S. P., . . . & Mucher, M. (2014). 2012 Anthropometric survey of US Army personnel: Methods and summary statistics (No. NATICK/TR-15/007). Army Natick Soldier Research Development and Engineering Center MA.

Thorborg, K, Bandholm, T., & Hölmich, P. (2013). Hip-and knee-strength assessments using a hand-held dynamometer with external belt-fixation are inter-tester reliable. Knee Surgery, Sports Traumatology, Arthroscopy, 21 (3), 550-555.

* cited by examiner

APPARATUS FOR MEASURING ISOMETRIC MUSCLE STRENGTH

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

FIELD OF THE INVENTION

The present invention relates to an apparatus for measuring isometric muscle strength.

BACKGROUND

Measurement of muscle strength is important in evaluating the fitness and strength of individuals. Measurement of muscle strength is also necessary during rehabilitation in order to evaluate treatment outcomes. Conventional machines for measuring muscle strength include the commercially available Cybex® and Biodex® machines. Both of these machines are well-established and effective. However, both of these commercially available machines have several disadvantages. One such disadvantage is that both machines require electrical power in order to function. Another disadvantage is that both machines are not easily transportable because they are heavy and bulky. Furthermore, both machines require controlled lab environments. Other conventional devices have been developed to address some of the disadvantages of the aforementioned conventional machines. One such conventional device is the portable, hand-held dynamometer (HHD). The HHD is a small, battery-powered, force measuring device that is commonly used today and has been a reliable technology for measuring isometric muscle strength in clinical environments when used by an experienced clinician. Typically, the researcher or clinician holds the HHD steady while the participant pushes against it using the appropriate muscle group. However, the results of measuring muscle strength with an HHD are influenced by the participant's body position, the ability to isolate the desired muscle group to be tested, placement location of the HHD and the skill of the researcher or clinician. Currently, there is no device or machine that allows the researcher to position the participant in a way that isolates the muscle group, or allows the researcher to stabilize the HHD in the event that the participant being tested has greater strength than the researcher. In order to address these disadvantages, researchers have developed techniques requiring belts and/or straps to aid in evaluating a specific muscle group. However, none of these techniques cover multiple muscle groups with the same set-up. Furthermore, these belt and strap techniques are not self-contained and cannot be performed in any location.

What is needed is a new apparatus for measuring isometric muscle strength that overcomes all of the disadvantages associated with conventional machines, devices and techniques.

SUMMARY OF THE INVENTION

The present invention is directed to an apparatus for measuring isometric muscle strength that overcomes the disadvantages of the foregoing conventional machines and techniques. The apparatus of the present invention is configured to isolate a muscle group in an individual or participant and provide a supported location for placement of a force-measuring device, such as a hand-held dynamometer, in order to accurately measure the muscle contraction. The present invention allows an adult researcher or clinician of any stature or strength to collect maximal isometric muscle strength metrics using the hand-held dynamometer on an adult participant of any stature or strength. The force-measuring device requires electrical power via one or more batteries, but the remaining components of the apparatus of the present invention do not require electrical power. The apparatus of the present invention is portable and is easily transported to different indoor or outdoor locations. The present invention is quickly deployed on any reasonably level surface and allows a researcher to secure a participant in a seated position for the purposes of isolating a muscle group of interest. The apparatus also allows the researcher to position and support the force-measuring device in a location that will accurately record the force exerted by the participant without requiring great strength on the part of the researcher.

Accordingly, in some embodiments, the present invention is directed to an apparatus for measuring the isometric muscle strength of various muscle groups in an individual. The apparatus comprises a table section having a top surface and a plurality of legs that support the top surface. The top surface has a front edge and a rear edge and is adapted to allow an individual or participant to sit thereon. A generally upright frame section is adjustably attached to the table section and spans the top surface of the table section. The frame section is configured for bi-directional movement over the top surface of the table section such that the frame section is movable toward the front edge or toward the rear edge. The frame section includes an open area above the top surface of the table section that is sized to allow a participant's legs and thighs to extend therethrough while the participant is seated on the top surface. At least one movement-impeding device is adjustably attached to the frame section and is configurable to a first state to prevent movement of the frame section and to a second state that allows movement of the frame section. A cradle is movably attached to the generally upright frame section and configured to hold a force-measuring device. The cradle has a front opening and is vertically movable upward and downward. A plurality of restraining devices are attached to the table section and configured to be secured to various parts of the participant's body to stabilize the participant on the top surface of the table section and to isolate muscle groups that are to be tested. In some embodiments, a force-measuring device is secured within the cradle. The force-measuring device has a sensor that protrudes from the front opening of the cradle so that it can be acted upon by a participant's body segment when the participant is sitting on the top surface of the table section.

In some embodiments, the invention is directed to an apparatus for measuring isometric muscle strength of various muscle groups in an individual. The apparatus comprises a table section having a top surface and a plurality of legs that support the top surface. The top surface has a front edge and a rear edge and is adapted to allow a participant to sit thereon. The table section has a first lengthwise end on one side of the table section and a second lengthwise end on an opposite side of the table section. The table section further comprises a first track attached to first lengthwise end of the table section and a second track attached to the second lengthwise end of the table section. A generally upright frame section is slidably attached to the first track and second track and spans the top surface of the table section. The frame section is configured for bi-directional movement over the top surface of the table section such that the frame section is slidable toward the front edge or toward the rear edge. The frame section has an open area above the top surface of the table section that is sized to allow a participant's legs and thighs to extend therethrough while the participant is seated on the top surface. A plurality of movement-impeding devices are adjustably attached to the frame section and are configurable to engage the first and second tracks to prevent movement of the frame section and are also configurable to disengage the first and second tracks to allow movement of the frame section. A cradle is movably attached to the generally upright frame section and configured to hold a force-measuring device. The cradle is movable in an upward direction or a downward direction. A force-measuring device is secured within the cradle and includes a sensor that protrudes from the front opening of the cradle so that it can be acted upon by a participant's body segment when the participant is sitting on the top surface of the table section. A plurality of belts or straps are attached to various portions of the table section and configured to be secured to various parts of the participant's body to stabilize the participant on the top surface of the table section and to isolate muscle groups that are to be tested for isometric muscle strength.

Certain features and advantages of the present invention have been generally described in this summary section. However, additional features, advantages and embodiments are presented herein or will be apparent to one of ordinary skill of the art in view of the drawings, specification and claims hereof. Accordingly, it should be understood that the scope of the invention shall not be limited by the particular embodiments disclosed in this summary section.

DETAILED DESCRIPTION OF EXEMPLARY EMBODIMENTS OF THE INVENTION

As used herein, the terms "comprises", "comprising", "includes", "including", "has", "having" or any other variation thereof, are intended to cover a non-exclusive inclusion. For example, a process, method, article or apparatus that comprises a list of elements is not necessarily limited to only those elements, but may include other elements not expressly listed or inherent to such process, method, article or apparatus.

It is to be understood that throughout this description, terms such as "vertical", "horizontal", "top", "bottom", "upper", "lower", "middle", "above", "below", "left", "right" and the like are used for convenience in identifying relative locations of various components and surfaces relative to one another in reference to the drawings and that the apparatus of the present invention may be installed and used in substantially any orientation so that these terms are not intended to be limiting in any way.

Approximating language, as used herein throughout the specification and claims, may be applied to modify any quantitative representation that could permissibly vary without resulting in a change in the basic function to which it is related. Accordingly, a value modified by a term such as "about" or "approximately" is not limited to the precise value specified.

As used herein, the term "participant" shall mean an individual or person that is to undergo isometric muscle testing. The term "participant" shall include athletes, medical patients and individuals that are in rehabilitation programs.

As used herein, the terms "researcher" or "clinician" shall refer to a person that is conducting the isometric muscle testing on the participant and includes scientists, medical personal, physical therapists, orthopedic specialists and chiropractors.

Figure 1:
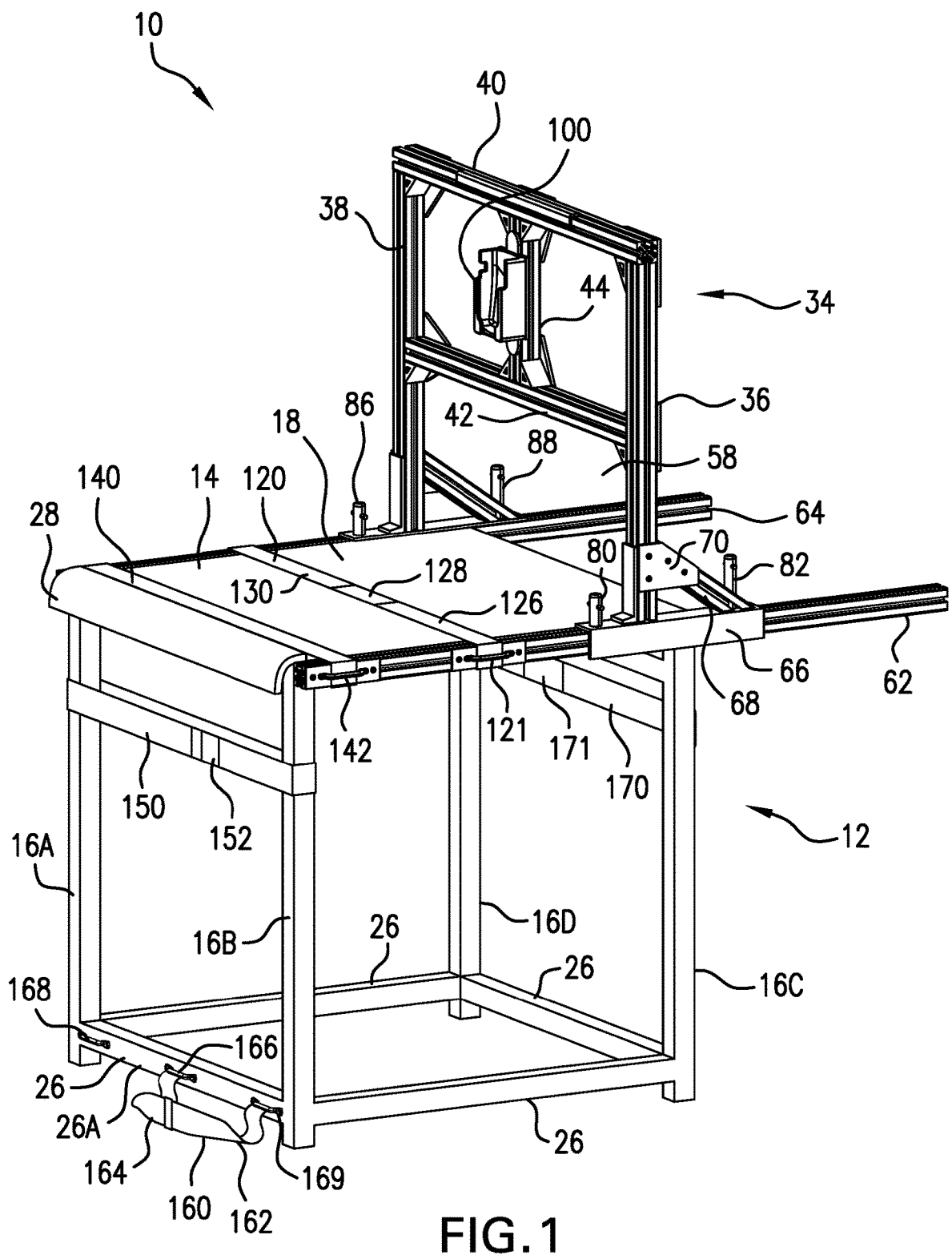
FIG. 1 is a perspective view of an apparatus for measuring isometric muscle strength in accordance with an exemplary embodiment of the present invention, the view showing the front and left sides of the apparatus.
Figure 2:
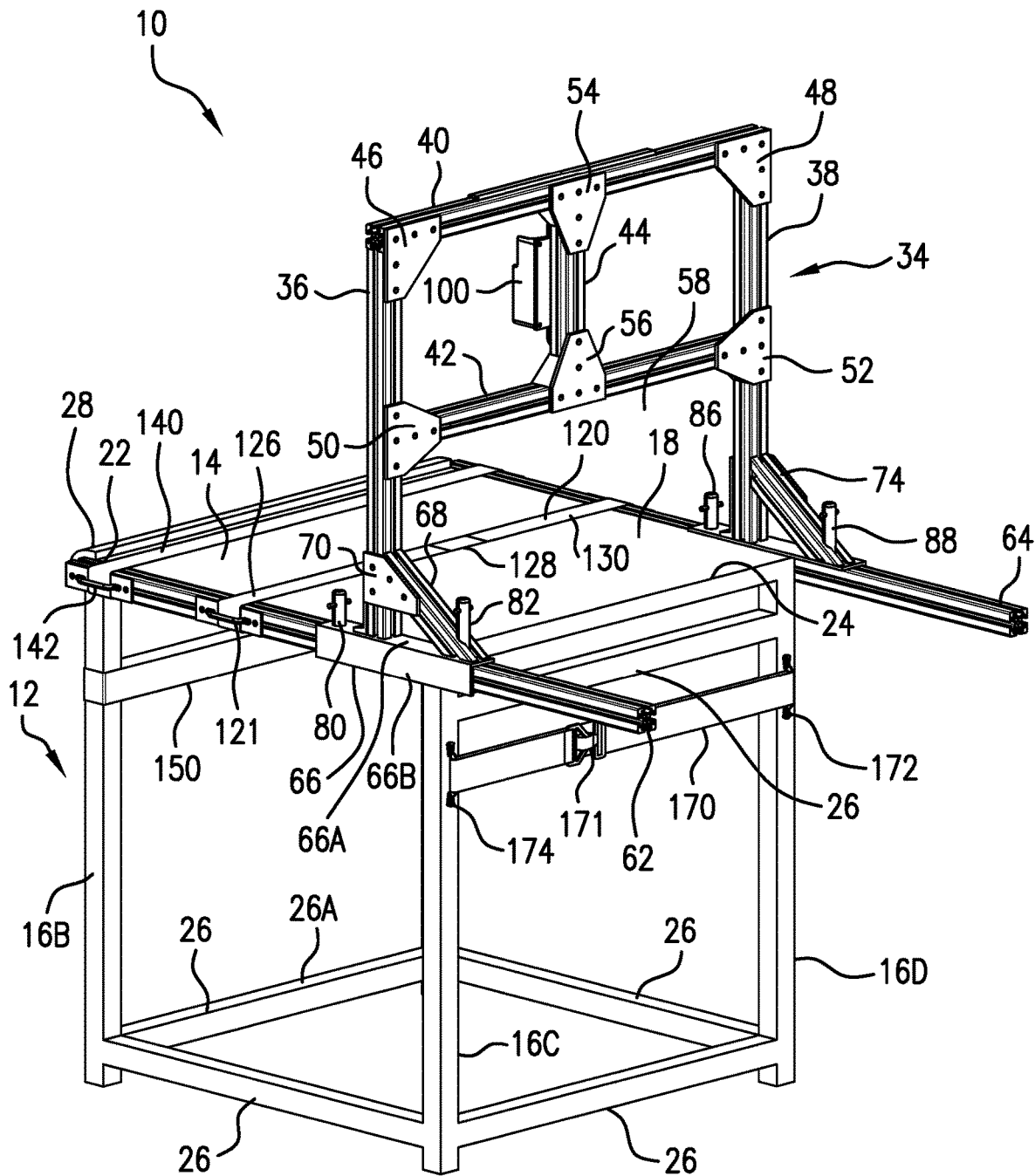
FIG. 2 is another perspective view of the apparatus for measuring isometric muscle strength, the view showing the rear and left sides of the apparatus.
Figure 8:
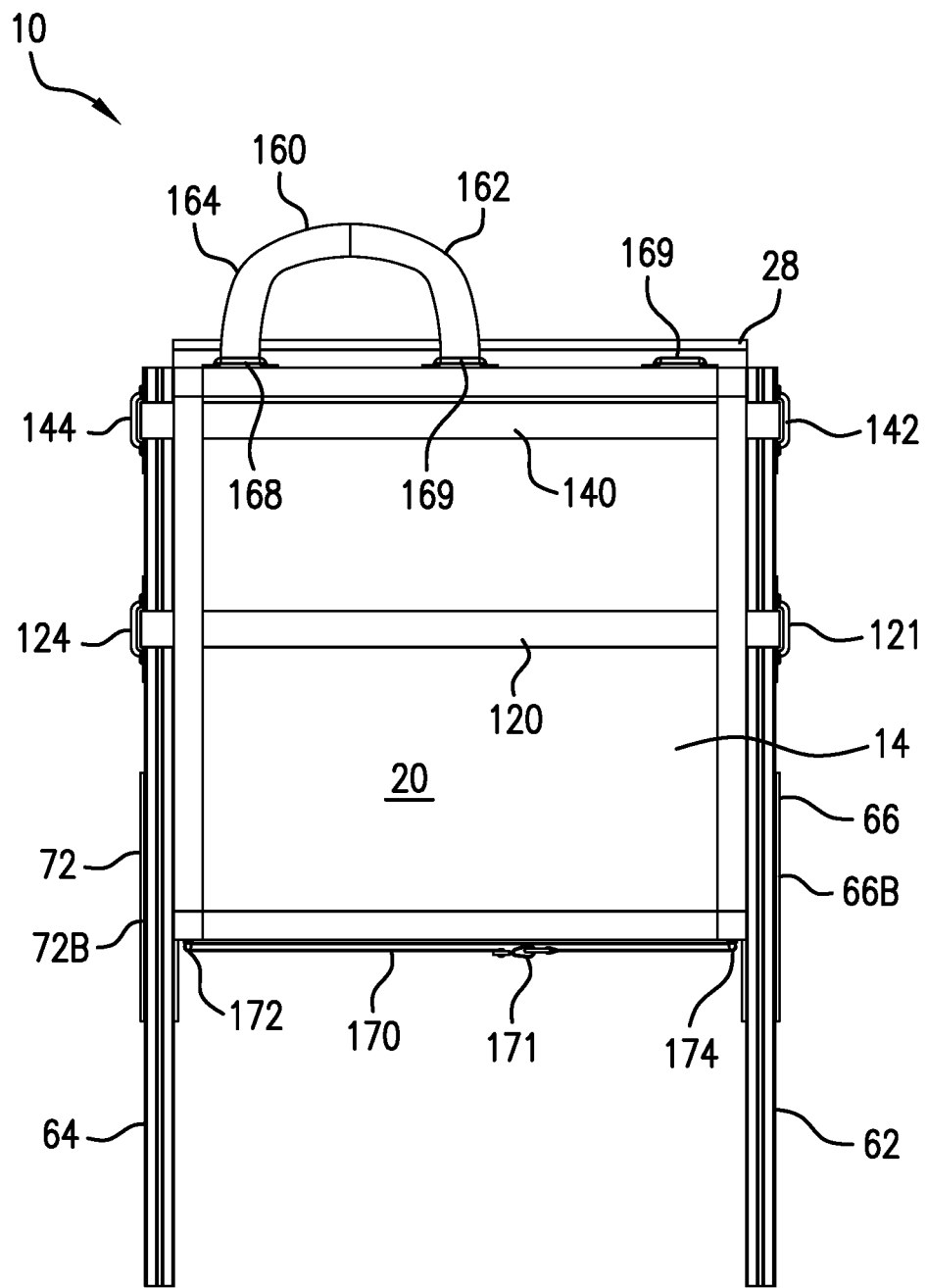
FIG. 8 is a bottom plan view of the apparatus for measuring isometric muscle strength.

Referring to FIGS. 1 and 2, there is shown apparatus 10 for measuring isometric muscle strength in accordance with an exemplary embodiment of the present invention. Apparatus 10 comprises table section 12 which includes generally horizontal section 14 and a plurality of leg members 16A, 16B, 16C and 16D that are attached to and support generally horizontal section 14. Horizontal section 14 has top surface 18 and bottom surface 20 (see FIG. 8). Top surface 18 has front edge 22 and rear edge 24. When apparatus 10 is in use, participant 60 sits upon top surface 18 in such a manner that his or her legs hang over either front edge 22 or rear edge 24, depending upon how participant 60 is seated upon top surface 18. The muscle group that is to be tested determines the position in which participant 60 sits upon top surface 18. Table section 12 further includes lateral support members 26 that are attached to leg members 16A, 16B, 16C and 16D and provide structural integrity to table section 12. Lateral support member 26A is attached to front leg members 16A and 16B. As shown in FIGS. 1, 2, 4 and 5, curved member 28 is attached or mounted to front edge 22 by any suitable means and is adapted to uniformly contact the area behind the knees of participant 60 so as to reduce discomfort when the participant is seated upon top surface 18. In an exemplary embodiment, curved member 28 comprises a neoprene sheath. In such an embodiment, the neoprene sheath has a thickness of about 0.5 inch. In some embodiments, fasteners (not shown) are used to attach curved member 28 to front edge 22. In some embodiments, an additional curved member, similar to curved member 28, is mounted or attached to rear edge 24 by any suitable means.

In some embodiments, leg members 16A-D are pivotally or hingedly attached to table section 12 and lateral support members 26 are removably attached to leg members 16A-D thereby allowing apparatus 10 to be folded up when not being used. Such a feature facilitates transportation and storage of apparatus 10.

In some embodiments, generally horizontal section 14 is fabricated from metal and top surface 18 is therefore metal. In some embodiments, generally horizontal section 14 is fabricated from metal and a layer of rubber is disposed over the metal such that top surface 18 is rubber. In such an embodiment, the layer of rubber on top surface 18 prevents participant 60 from sliding or moving while the isometric muscle testing is ongoing. In some embodiments, generally horizontal section 14 is fabricated from rubber and top surface 18 is therefore rubber. In other embodiments, other suitable materials are used to fabricate generally horizontal section 14.

Table section 12 has first lengthwise end 30 which is on the left side of table section 12 and second lengthwise end 32 which is on the right side of table section 12. In an exemplary embodiment, table section 12 has a square shape and each side of table section 12 has a length of about 30 inches. In an exemplary embodiment, table section 12 has a height of about 30 inches.

Figure 10:
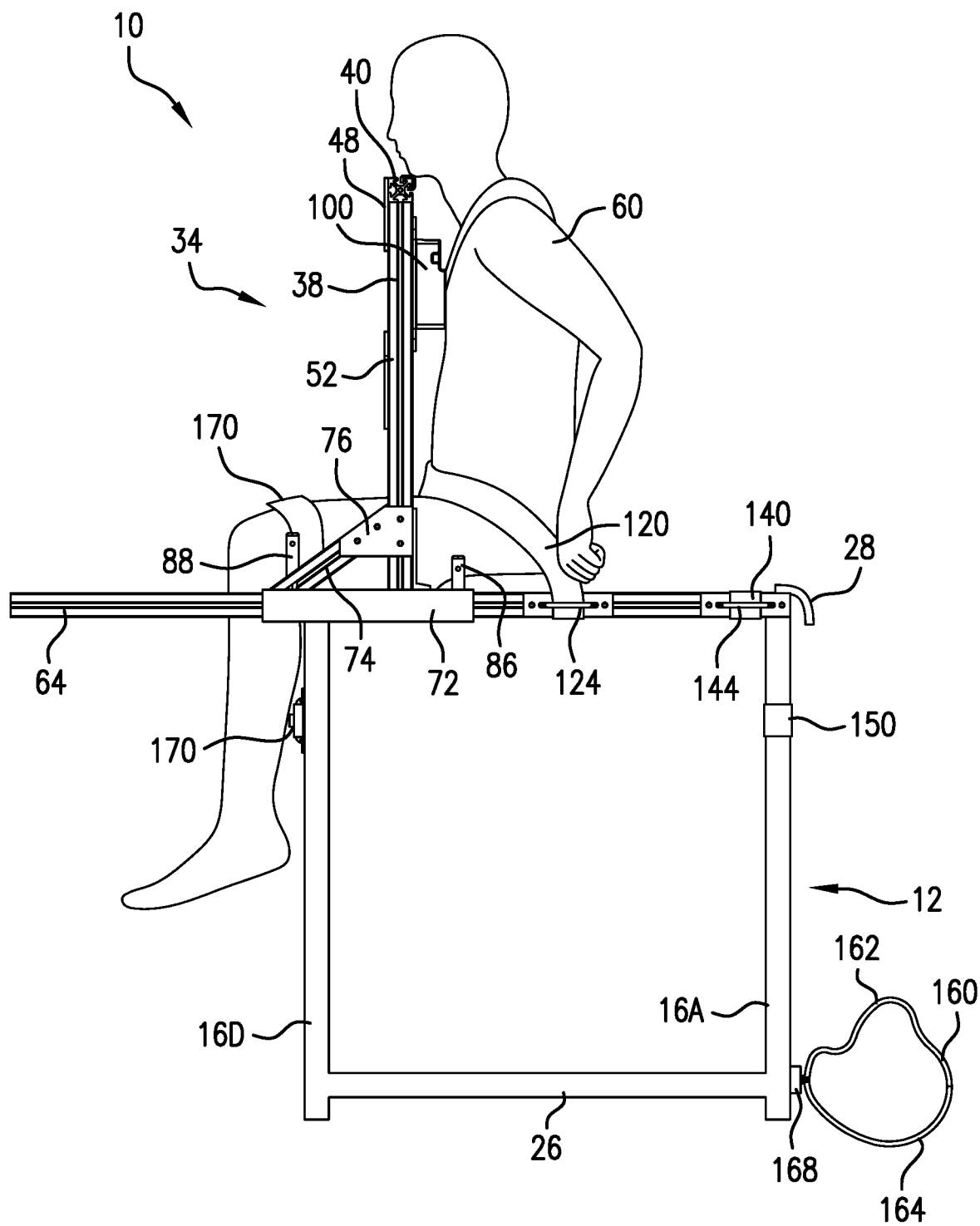
FIG. 10 is a right side elevational view of the apparatus for measuring isometric muscle strength, the view showing a participant positioned to enable measurement of the isometric muscle strength of the lumbar flexion muscles.
Figure 11:
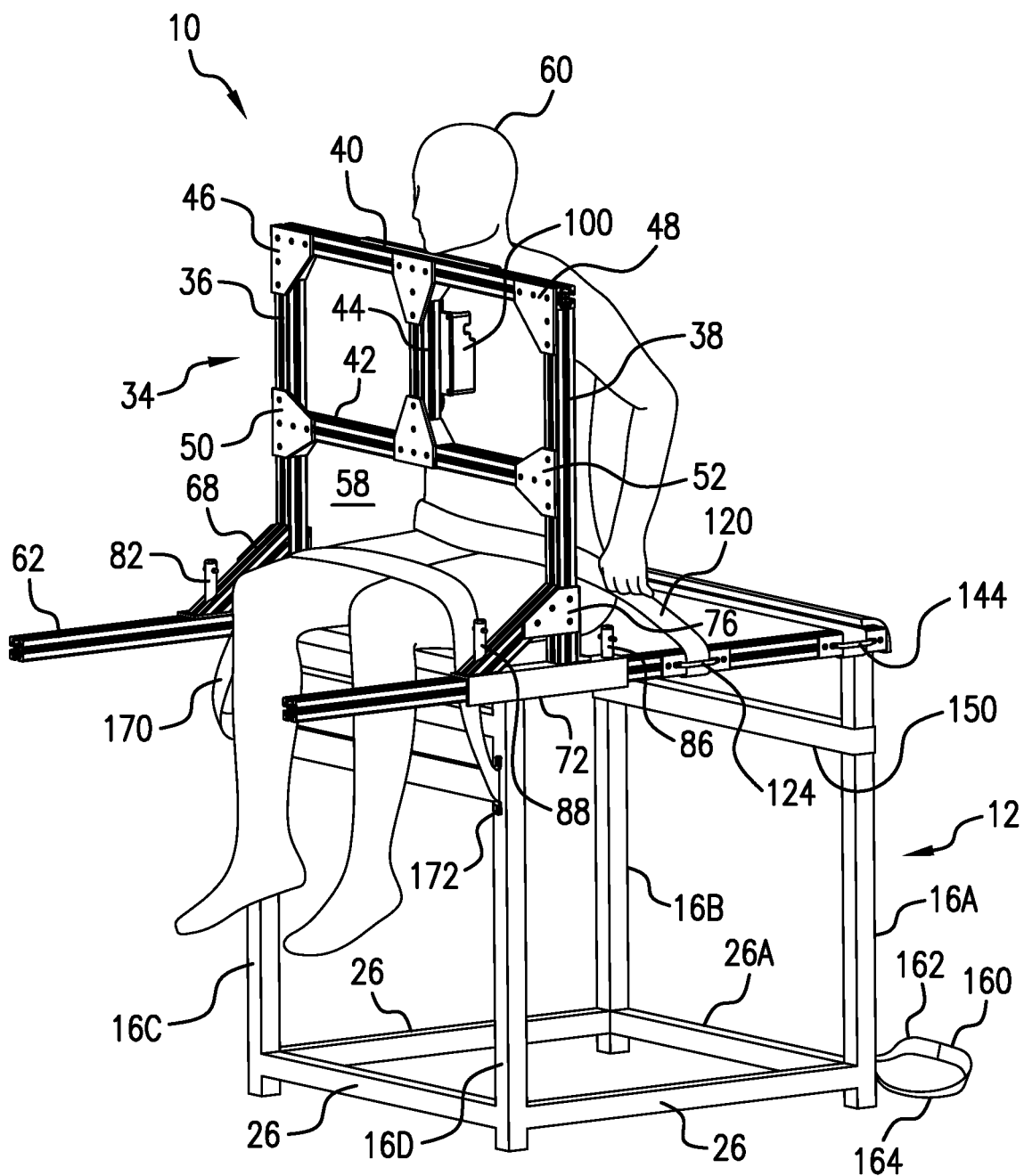
FIG. 11 is perspective view of the apparatus for measuring the isometric muscle strength with the participant positioned to enable measurement of the isometric muscle strength of the lumbar flexion muscles.
Figure 12A:
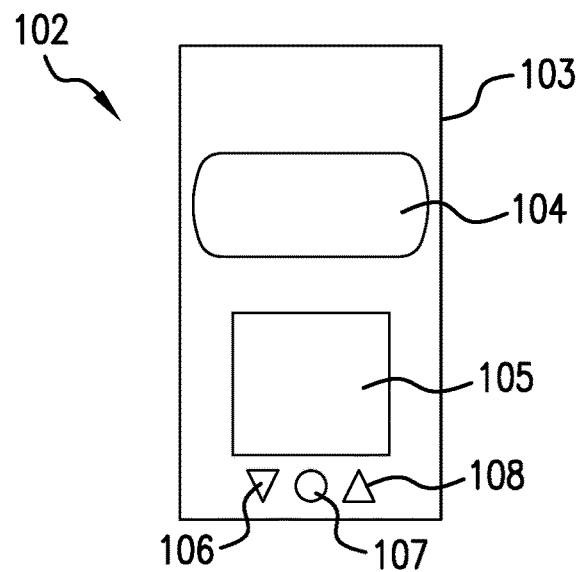
FIG. 12 A is a front elevational view of one embodiment of a force-measuring device that may be used with the apparatus for measuring isometric muscle strength.
FIG. 12B is a perspective front view of a cradle that is shown in FIGS. 1-11 and is configured to hold the force-measuring device.
Figure 12B:
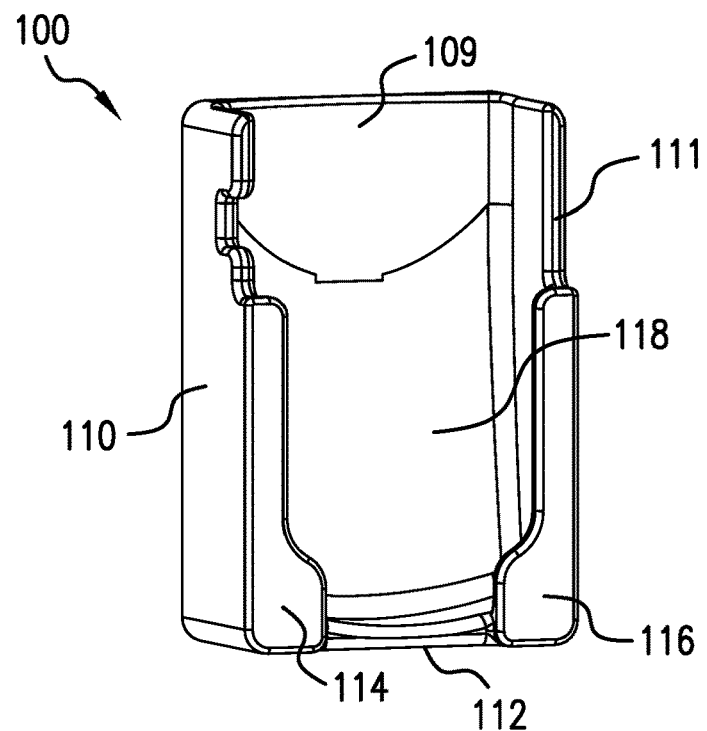
Figure 13:
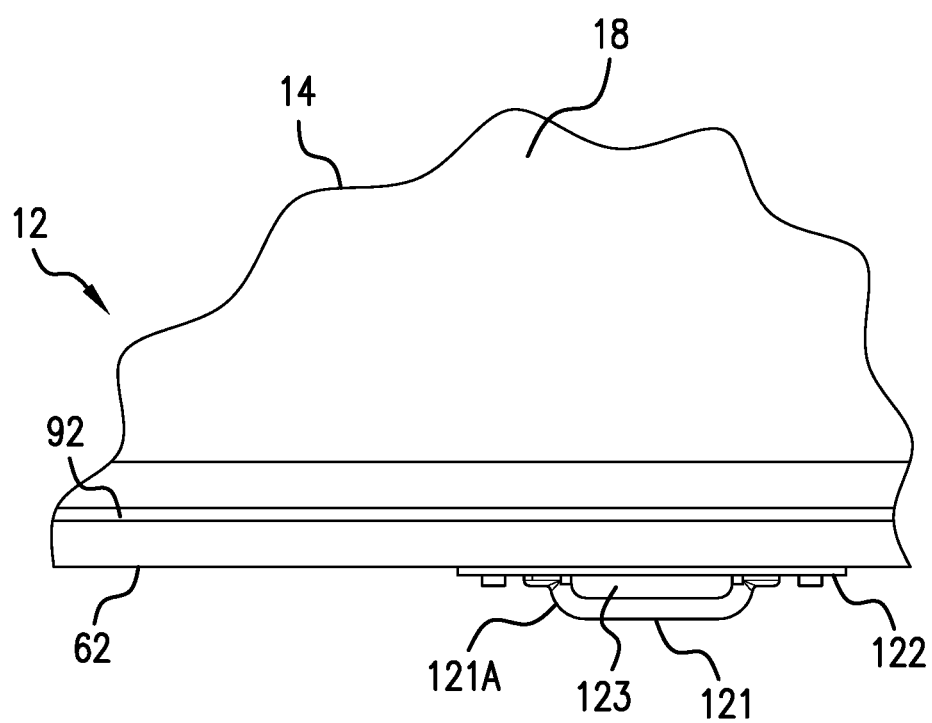
FIG. 13 is a partial, top view of the table section shown in FIGS. 1-11, the view also showing a belt support member attached to the side of the table section.

As shown in FIGS. 1-7, apparatus 10 further comprises generally upright frame section 34. Frame section 34 is adjustably attached to table section 12. Frame section 34 spans top surface 18 of table section 12 and is configured for bi-directional movement over top surface 18. Frame section 34 is movable toward front edge 22 or toward rear edge 24. Frame section 34 comprises vertical members 36 and 38 which are in proximity to first lengthwise end 30 and second lengthwise end 32, respectively. In an exemplary embodiment, vertical members 36 and 38 are substantially perpendicular to top surface 18. Frame section 34 includes top lateral support member 40 that is attached to vertical members 36 and 38. Frame section 34 further includes bottom lateral support member 42. In an exemplary embodiment, lateral support members 40 and 42 are substantially horizontal such that bottom lateral support member 42 is substantially parallel to top lateral support member 40. Frame section 34 includes vertical member 44 that is attached to both top lateral support member 40 and bottom lateral support member 42. The midpoints of top lateral support member 40 and bottom lateral support member 42 are aligned with the midpoint of top surface 18. Vertical member 44 is located at the midpoints of top lateral support member 40 and bottom lateral support member 42. Hence, vertical support member 44 is also aligned with the midpoint of top surface 18. Top lateral support member 40 is attached to vertical members 36 and 38 via support plates 46 and 48, respectively. Similarly, bottom lateral support member 42 is attached to vertical members 36 and 38 via support plates 50 and 52, respectively. In some embodiments, fasteners such as screws, bolts, rivets or similar fasteners are used to connect support plate 46 to vertical member 36 and top lateral support member 40 and to connect support plate 48 to vertical member 38 and top lateral support member 40. Similarly, in some embodiments, fasteners such as screws, bolts, rivets or similar fasteners are used to connect support plate 50 to vertical member 36 and bottom lateral support member 42 and to connect support plate 52 to vertical member 38 and bottom lateral support member 42. Vertical member 44 is attached to top lateral support member 40 via support plate 54 and to bottom lateral support member 42 via support plate 56. Any of the fasteners previously described may be used to attach the support plates 54 and 56. As shown in FIGS. 1, 2 and 11, frame section 34 has an opening 58 that is below bottom lateral support member 42 and above top surface 18 of table section 12. Opening 58 is sized to allow participant 60 to insert his or her legs and thighs therethrough while participant 60 is seated on top surface 18 in an opposing relationship to frame section 34, as shown in FIG. 10, such that the participant's sternum opposes the front side of frame section 34. The purpose for participant 60 being positioned as shown in FIG. 10 is described in detail in the ensuing description.

Figure 3:
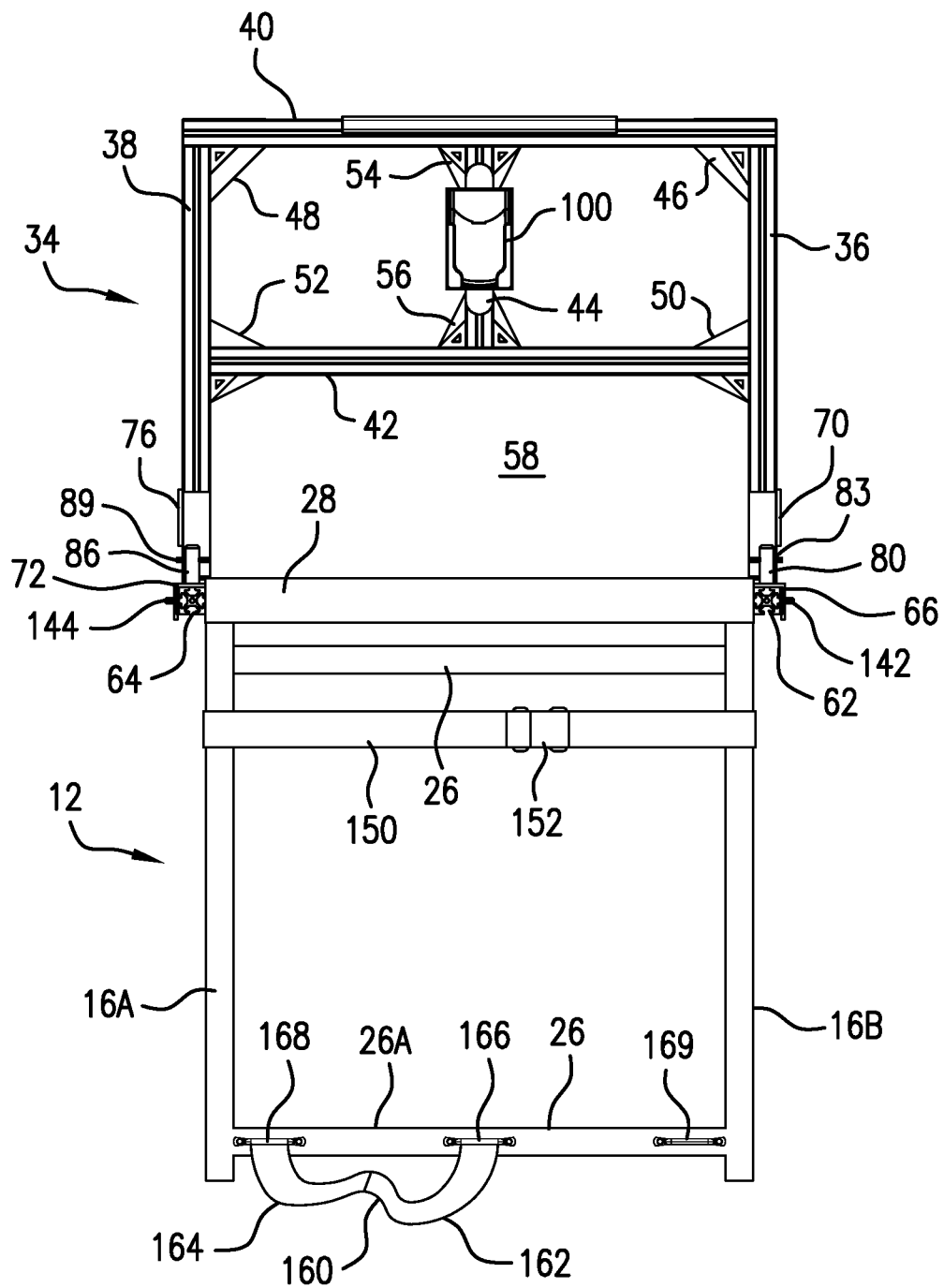
FIG. 3 is a front elevational view of the apparatus for measuring isometric muscle strength.
Figure 6:
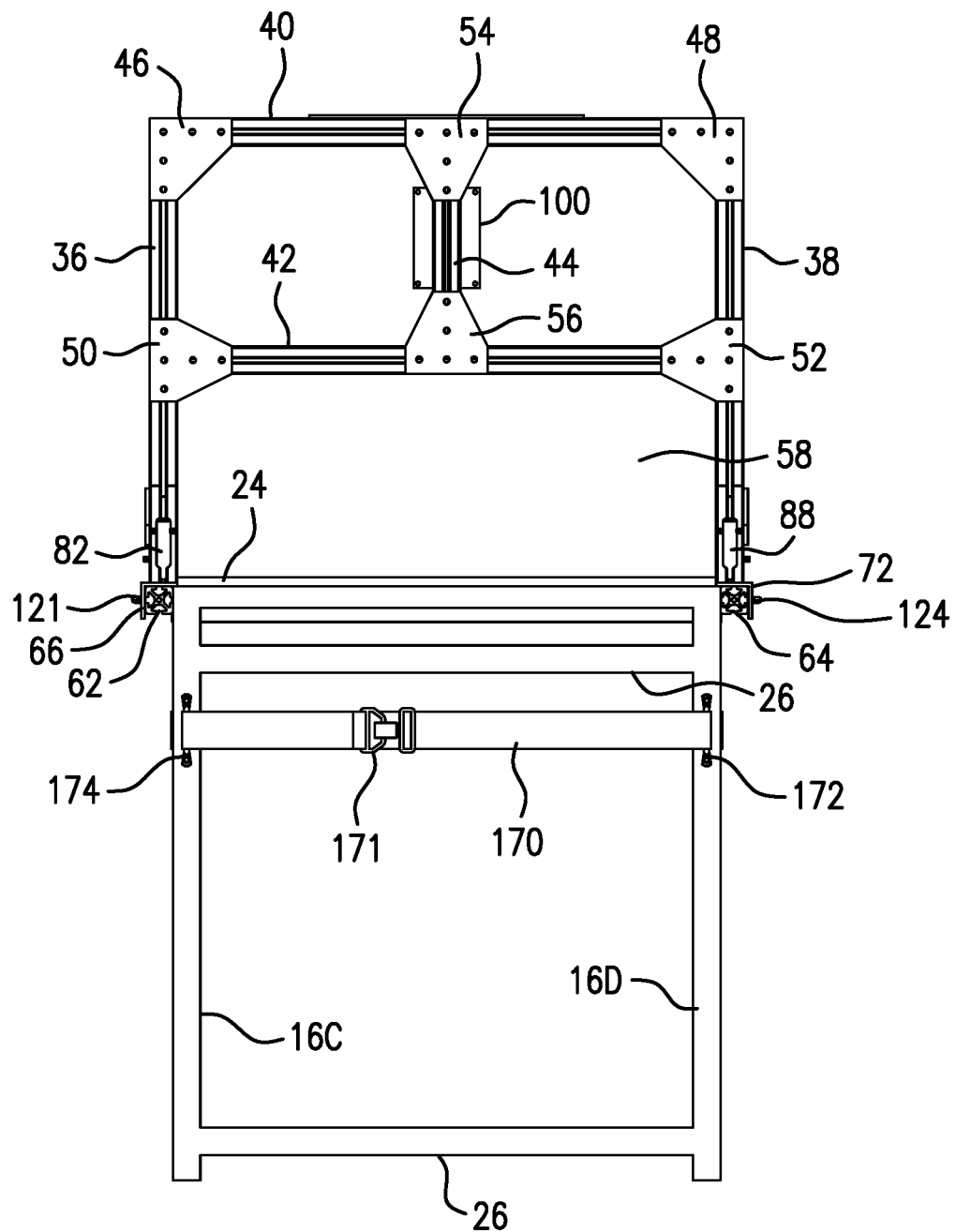
FIG. 6 is a rear side elevational view of the apparatus for measuring isometric muscle strength.
Figure 7:
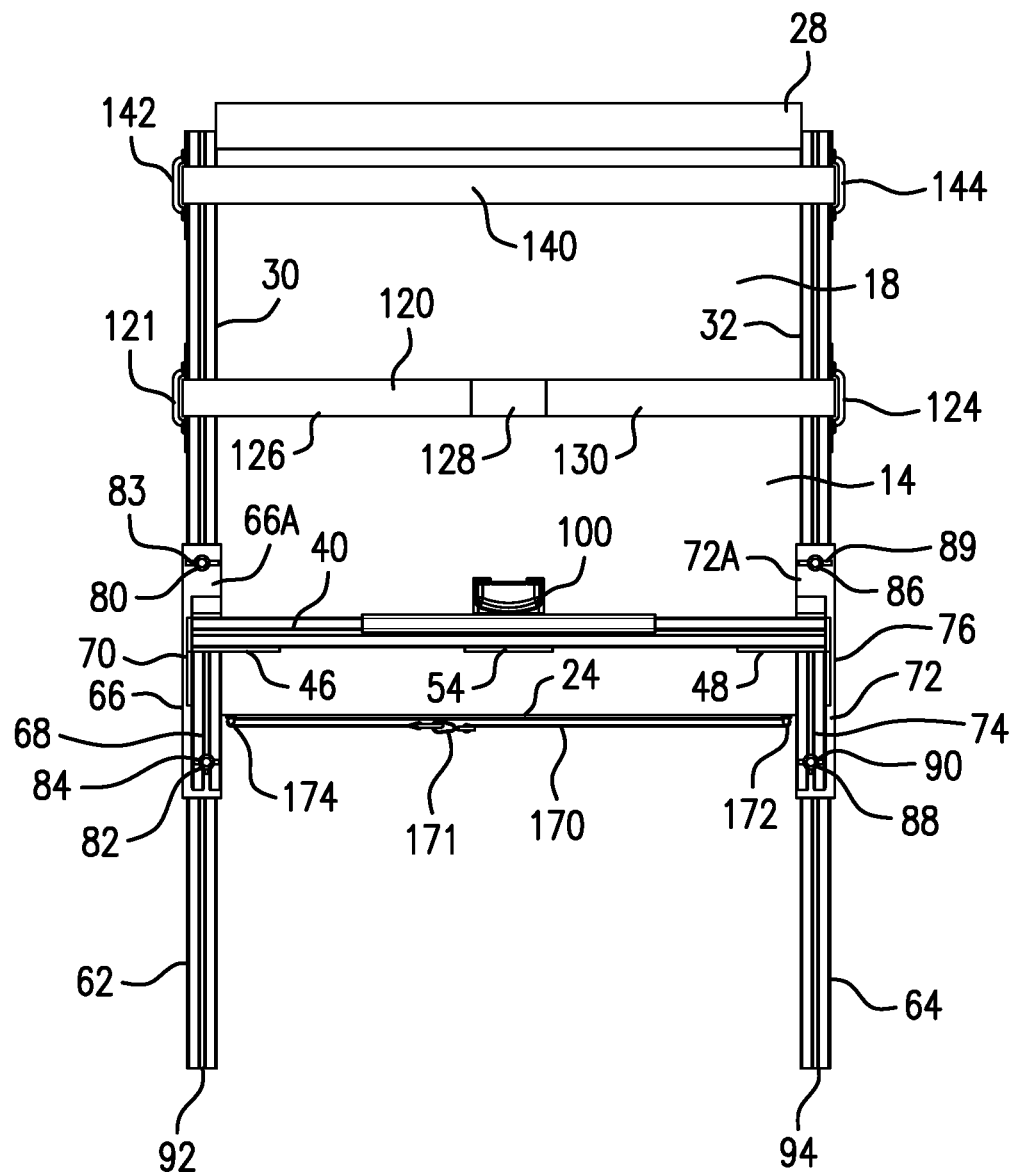
FIG. 7 is a top plan view of the apparatus for measuring isometric muscle strength.

Referring to FIGS. 1-7, table section 12 further comprises track 62 that is attached to table section 12 at first lengthwise end 30. Table section 12 further comprises track 64 that is attached to table section 12 at second lengthwise end 32. Tracks 62 and 64 extend beyond rear edge 24. Frame section 34 further comprises bracket 66 that is attached to the bottom end of vertical member 36 and is slidably mounted on track 62. As shown in FIG. 3, bracket 66 comprises section 66A and section 66B. Section 66B is substantially perpendicular to section 66A. Any suitable method may be used to attach the bottom end of vertical member 36 to bracket 66. In some embodiments, the bottom end of vertical member 36 is welded to bracket 66. In other embodiments, fasteners or similar devices are used to attach bottom end of vertical member 36 to bracket 66. Support member 68 is attached to vertical member 36 and bracket 66 so as to provide structural integrity to frame section 34. In an exemplary embodiment, support member 68 is positioned at a 45° angle with respect to bracket 66. However, support member 68 may be positioned at other suitable angles. Support plate 70 is used to attach support member 68 to vertical member 36. Frame section 34 further comprises bracket 72 which is attached to the bottom end of vertical member 38 and slidably mounted on track 64. As shown in FIGS. 3 and 7, bracket 72 comprises section 72A and section 72B. Section 72B is substantially perpendicular to section 72A. Any suitable method may be used to attach the bottom end of vertical member 38 to bracket 72. In some embodiments, the bottom end of vertical member 38 is welded to bracket 72. Support member 74 is attached to vertical member 38 and bracket 72 so as to provide structural integrity to frame section 34. In an exemplary embodiment, support member 74 is positioned at a 45° angle with respect to bracket 72. However, support member 74 may be positioned at other suitable angles. Support plate 76 is used to attach support member 74 to vertical member 38. As a result of this structural configuration, frame section 34 slides on tracks 62 and 64 in a first direction toward front edge 22 or in an opposite, second direction toward rear edge 24.

Referring to FIGS. 1 and 2, apparatus 10 further comprises movement-impeding devices 80 and 82 that are adjustably attached to section 66A of bracket 66. In some embodiments, each movement-impeding device 80 and 82 comprises a threaded member that is threadedly engaged with a corresponding threaded thru-hole or opening in section 66A. In an exemplary embodiment, each threaded member has a generally cylindrical shape. As shown in FIG. 2, movement-impeding device 82 extends through an opening (not shown) in support member 68 and is threadedly engaged to the aforementioned threaded thru-hole in section 66A of bracket 66. Movement-impeding device 80 includes generally horizontal pin 83 that extends through the top portion of movement-impeding device 80 (see FIG. 7). Pin 83 facilitates rotation of movement-impeding device 80. Similarly, movement-impeding device 82 includes generally horizontal pin 84 that extends through the top portion of movement-impeding device 82. Pin 84 facilitates rotation of movement-impending device 82. In order to prevent bracket 66 from moving on track 62, the researcher rotates movement-impeding devices 80 and 82 until the devices physically contact or engage track 62. Apparatus 10 further comprises movement-impeding devices 86 and 88 that are adjustably attached to section 72A of bracket 72. In some embodiments, each movement-impeding device 86 and 88 comprises a threaded member that is threadedly engaged with a corresponding threaded thru-hole or opening in section 72A. In an exemplary embodiment, each threaded member has a generally cylindrical shape. As shown in FIG. 2, movement-impeding device 88 extends through an opening (not shown) in support member 74 and is threadedly engaged to the aforementioned threaded thru-hole in section 72A of bracket 72. Movement-impeding device 86 includes generally horizontal pin 89 that extends through the top portion of movement-impeding device 86 (see FIG. 7). Pin 89 facilitates rotation of movement-impeding device 86. Similarly, movement-impeding device 88 includes generally horizontal pin 90 that extends through the top portion of movement-impeding device 88. Pin 90 facilitates rotation of movement-impeding device 88. In order to prevent bracket 72 from moving upon track 64, the researcher rotates movement-impeding devices 86 and 88 until the devices physically contact or engage track 64. In order to slide frame section 34 in the direction of front edge 22 or in the direction of rear edge 24, the researcher rotates devices 80, 82, 86 and 88 counter-clockwise in order to break the physical contact between track 62 and devices 80 and 82, and break the physical contact between track 64 and devices 86 and 88. In order to fix frame section 34 at a particular location on tracks 62 and 64, the researcher rotates movement-impeding devices 80 and 82 clockwise until these devices physically contact track 62 and also rotates movement-impeding devices 86 and 88 clockwise until these devices physically contact track 64. Once movement-impeding devices 80 and 82 firmly contact track 62 and movement-impeding devices 86 and 88 firmly contact track 64, frame section 34 is fixed at that particular position.

Referring to FIG. 7, in an exemplary embodiment, track 62 and track 64 have longitudinally extending channels 92 and 94, respectively. As movement-impeding devices 80 and 82 are rotated clockwise, portions of devices 80 and 82 enter channel 92 and physically contact track 62 so as to lock bracket 66 in place. Similarly, as movement-impeding devices 86 and 88 are rotated clockwise, portions of devices 86 and 88 enter channel 94 and physically contact track 64 so as to lock bracket 72 in place.

Referring to FIGS. 1-3, 12A and 12B, apparatus 10 further comprises cradle or holder 100 for holding force-measuring device 102. Force-measuring device 102 is just one example of a force-measuring device that can be used with apparatus 10. It is to be understood that there are several suitable commercially available force-measuring devices that are described in the ensuing description and which may be used with apparatus 10. Force-measuring device 102 includes casing 103, sensor 104, display screen 105 and control buttons 106, 107 and 108. Force-measuring device 102 is further described in the ensuing description. Cradle 100 includes rear wall 109 and sidewalls 110 and 111 that are contiguous with rear wall 109. Cradle 100 includes bottom section 112 and front wall sections 114 and 116. Front wall sections 114 and 116 are contiguous with sidewalls 110 and 111, respectively. Front wall sections 114 and 116 are spaced apart by opening 118. Force-measuring device 102 rests upon bottom section 112 when force-measuring device 102 is positioned within cradle 100. Front wall sections 114 and 116 and bottom section 112 retain force-measuring device 102 within cradle 100. When force-measuring device 102 is positioned within cradle 100, sensor 104 protrudes or extends from opening 118 so as to facilitate physical contact with the participant's torso.

It is to be understood that cradle 100 as described in the foregoing description pertains to just one exemplary embodiment. Accordingly, cradle 100 may have any other suitable shape and geometry.

In some embodiments, cradle 100 is movably attached to vertical member 44 of frame section 34 such that cradle 100 is movable upward or downward. In one embodiment, vertical member 44 includes a track (not shown) and rear wall 109 of cradle 100 includes a protruding tab (not shown) that is engaged with the track on vertical member 44 so as to allow cradle 100 to slide upward or downward. In such an embodiment, vertical member 44 includes a locking device (not shown) to lock cradle 100 in the desired position.

In some embodiments, vertical member 44 includes a plurality of openings vertically arranged in a column and rear wall 109 of cradle 100 includes a tab or hook that is sized to fit into any of the openings in the column of openings. Such a configuration allows the researcher to vertically adjust cradle 100 to different positions depending upon the size or stature of participant 60.

In an exemplary embodiment, force-measuring device 102 is a commercially available hand-held dynamometer. Examples of suitable commercially available hand-held dynamometers are Lafayette Instrument's "Hand-Held Dynamometer", previously called the "Manual Muscle Testing (MMT) Device", Hoggan Scientific's "MicroFET 2 Manual Muscle Testing Dynamometer", JTECH's "Commander Echo Manual Muscle Testing Dynamometer", Biometrics LTD's "MyoMeter Handheld Dynamometer" and Baseline Evaluation Instruments' "Manual Muscle Tester".

Referring to FIGS. 1-3, 6, 7 and 9, apparatus 10 further comprises a plurality of restraining devices attached to table section 12 and adapted to secure the participant to top surface 18 and to isolate various muscle groups that are to be tested. The plurality of restraining devices comprises adjustable belt or strap 120 that is configured to hold or secure participant 60 during isometric muscle testing. Belt 120 extends over top surface 18, around first lengthwise end 30, across bottom surface 20, up and around second lengthwise end 32 and back to top surface 18. Belt 120 comprises belt sections 126, buckle 128 and belt section 130. In an exemplary embodiment, section 126 includes buckle 128 and section 130 includes a clip (not shown) that is configured for removable engagement with buckle 128 in order to lock sections 126 and 130 together. Buckle 128 includes a release mechanism (not shown) that when manipulated by the participant, releases the clip from buckle 128. Referring to FIGS. 1, 4, 5 and 13, apparatus 10 includes belt support member 121. Belt support member 121 includes loop portion 121A and plate member 122. Loop portion 121A is attached to plate member 122 and plate member 122 is movably attached to the outer side of track 62. In an exemplary embodiment, loop portion 121A is fabricated from a stiff material such as metal or plastic. Any suitable technique or method may be used to movably attach plate member 122 to the outer side of track 62. In some embodiments, fasteners, such as screws, are used to attach plate member 122 to track 62. Space or gap 123 exists between loop portion 121A and plate member 122. Belt 120 passes through space 123. Apparatus 10 further includes belt support member 124 which is movably attached to the exterior side of track 64 and has the same structure as belt support member 121. Accordingly, belt support member 124 also a space (not shown) that has the same purpose as space 123.

In some embodiments, belt 120 comprises a pair of Velcro® straps wherein one strap is attached to track 62 and the other strap is attached to track 64 and the straps are joined together at the participant's lower torso or upper thighs. In some embodiments, belt 120 comprises a parachute strap and buckle system. In some embodiments, buckle 128 comprises a Cobra® Quick Release Buckle.

Referring to FIGS. 2, 4, 5, 7 and 9, the plurality of restraining devices further comprises belt or strap 140. Belt 140 is positioned and adapted to be wrapped around the participant's thighs. Belt 140 passes through belt support members 142 and 144 that are movably attached to the sides of track 62 and track 64, respectively. Belt support members 142 and 144 have the same structure as belt support member 121. In an exemplary embodiment, belt 140 is a Velcro® belt. However, in other embodiments, belt 140 may be configured to have any of the buckles described in the foregoing description with respect to belt 120.

Referring to FIGS. 2, 3, 4 and 6, the plurality of restraining devices further comprises belt 150. Belt 150 is positioned so as to be wrapped around the shin portions of the participant's legs (see FIG. 9). In an exemplary embodiment, belt 150 is a Velcro® belt. In such an embodiment, portions of belt 150 are attached to the upper portion of front leg members 16A and 16B of table section 12. Any suitable technique or method may be used to attach the portions of belt 150 to front leg members 16A and 16B. Examples of such suitable techniques and methods include adhesives, tape, fasteners, etc. In some embodiments, belt 150 is configured to have any of the buckles described in the foregoing description with respect to belt 120.

Referring to FIG. 3, the plurality of restraining devices further comprises belt 160. Belt 160 is positioned so as to be wrapped around the top of the participant's foot (see FIG. 1). In an exemplary embodiment, belt 160 is a Velcro® belt that has complementary sections 162 and 164. In such an embodiment, one end of section 162 is attached to belt support member 166 which is attached to front lateral support member 26A of table section 12. Similarly, the opposite end of belt section 164 is attached to belt support member 168 which is also attached to front lateral support member 26A. The researcher fastens belt 160 to belt support members 166 and 168 in order to test the isometric muscle strength of the participant's right ankle. Additional belt support member 169 is also attached to front lateral support member 26A and allows belt 160 to be attached to belt support members 166 and 169 so the isometric muscle strength of the participant's left ankle can be tested. Belt support members 166, 168 and 170 have the same structure as belt support member 121 which was described in the foregoing description. In other embodiments, belt 160 may be realized by any of the other belts or straps described in the foregoing description.

Figure 4:
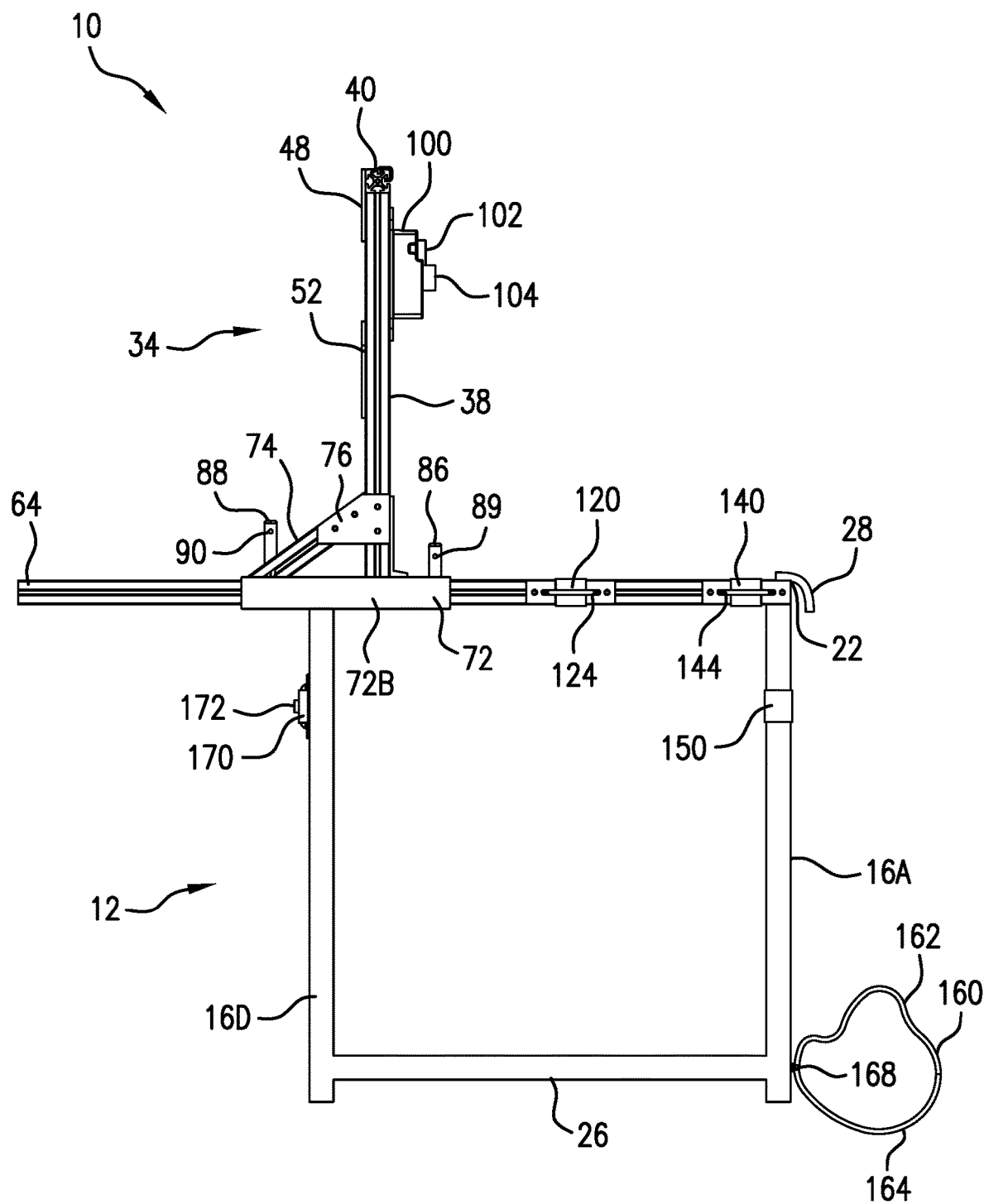
FIG. 4 is a right side elevational view of the apparatus for measuring isometric muscle strength.
Figure 5:
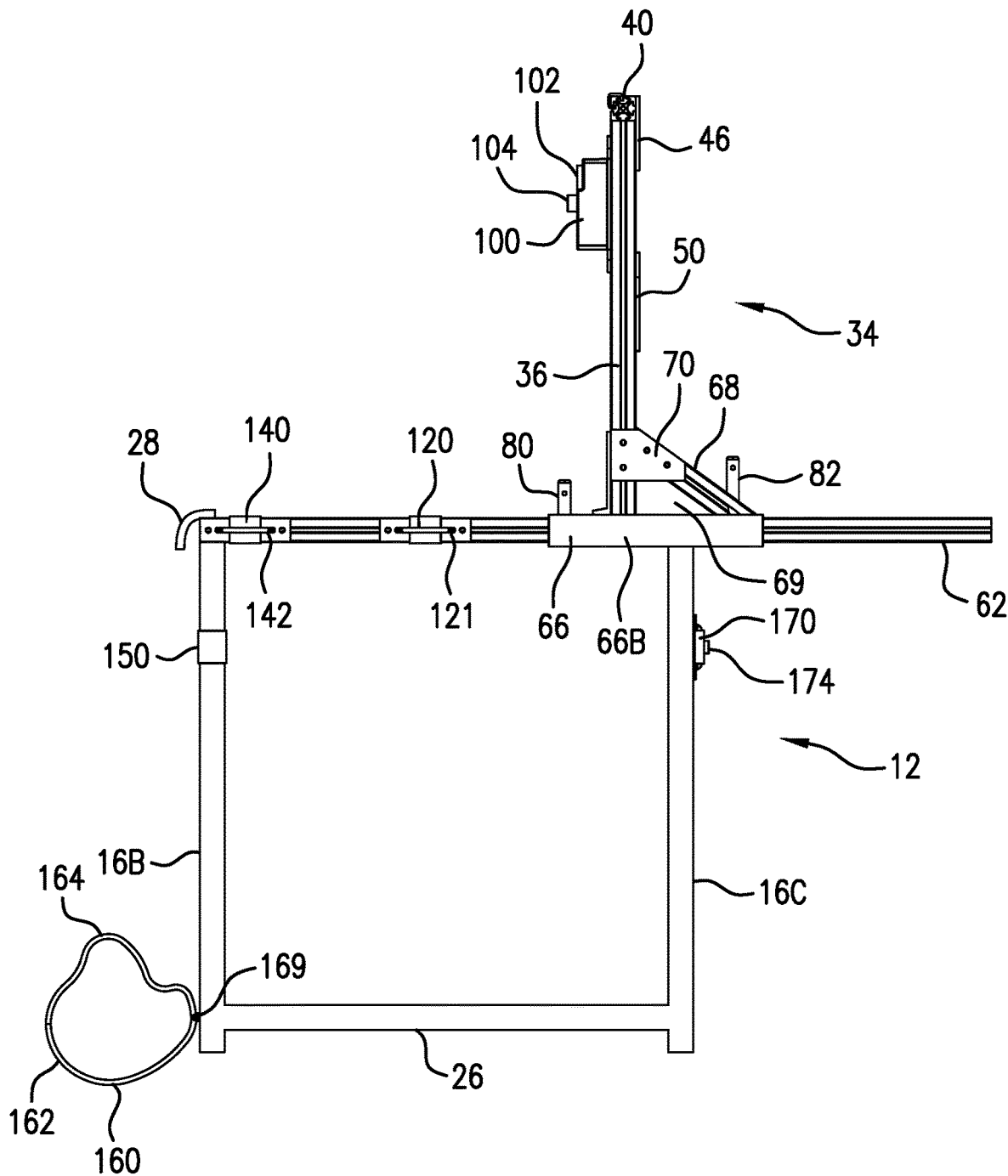
FIG. 5 is a left side elevational view of the apparatus for measuring isometric muscle strength.

Referring to FIGS. 2, 4 and 6, the plurality of restraining devices further comprises adjustable rear belt or strap 170. Rear belt 170 is supported by belt support members 172 and 174 which are attached to rear leg members 16D and 16C, respectively. Belt support members 172 and 174 have the same structure as belt support member 121 described in the foregoing description. Rear belt 170 extends through the belt support members 172 and 174 and has a length that allows belt 170 to pass over the participant's thighs as shown in FIG. 11. In an exemplary embodiment, rear belt 170 uses the same type of clip and buckle system as belt 120 which was described in the foregoing description. However, it is to be understood that any of the belt buckle devices described in the foregoing description may be used on rear belt 170.

Figure 9:
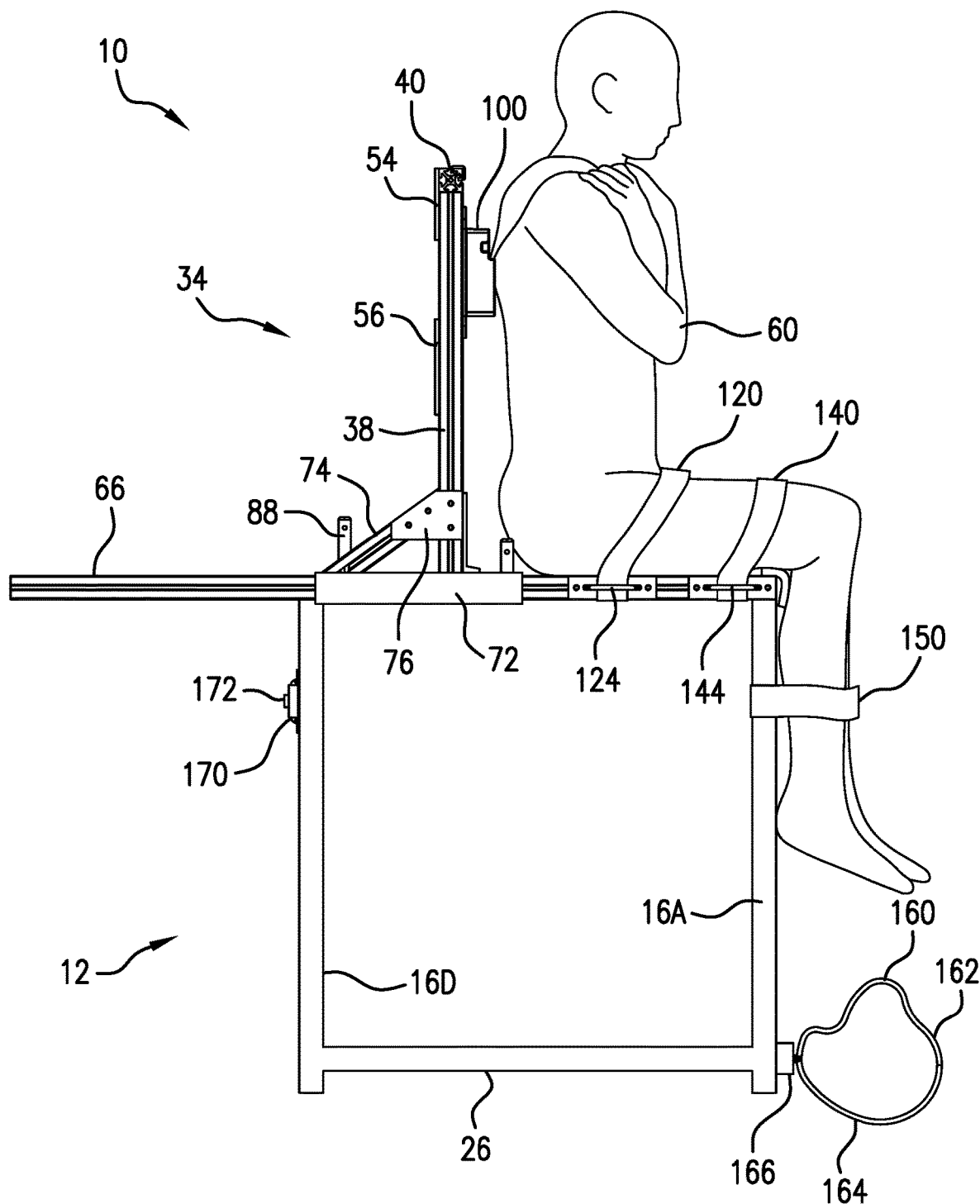
FIG. 9 is a right side elevational view of the apparatus for measuring isometric muscle strength, the view also showing a participant positioned to enable measurement of the isometric muscle strength of the lumbar extension muscles.

Apparatus 10 allows numerous tests to be conducted on different muscle groups to determine isometric muscle strength. In all of the tests described in the ensuing description, force-measuring device 102 is realized by a hand-held dynamometer (HHD). Prior to each test, the researcher sets up the HHD 102 according to the appropriate device instructions. Referring to FIG. 9, there is shown the test setup for testing the participant's lumbar extension muscles. The researcher first secures force-measuring device 102 in cradle or holder 100. Participant 60 is then seated on top surface 18 and positioned so that sensor 104 is aligned in the center of the participant's back, between the shoulder blades. Participant 60 is secured to table section 12 by belt 120. Belt 140 is secured about the participant's lower thighs and belt 150 is secured about the participant's legs in proximity to or at the shins. Belts 160 and 170 are not used in this test. Participant 60 then crosses his or her arms and places his or her hands in proximity to the shoulders. Participant 60 then presses his or her back into sensor 104 with as much force as possible. Participant 60 maintains this force until force-measuring device 102 indicates that sufficient data has been obtained. In some embodiments, force-measuring device 102 is configured to emit an audio sound such as tone or buzzer after sensor 104 is depressed for a predetermined amount of time.

FIGS. 10 and 11 illustrate the test setup for testing the participant's lumbar flexion muscles. In this test, participant 60 reverses his position on table section 12 so that his legs and thighs extend through open area 58 in frame section 34 and extend over rear edge 24. The researcher uses belt 120 to secure participant 60 to top surface 18. Rear belt 170 is then fastened about the participant's thighs. Sensor 104 is aligned with the center of the participant's sternum. Participant 60 then presses his sternum against sensor 104 with as much force as possible until force-measuring device 102 indicates that sufficient data has been obtained.

In order to test the participant's ankle dorsiflexion muscles, participant 60 sits on top surface 18 of table section 12 so that the participant's legs extend over front edge 22 and the back of the participant's knees contact curved surface 28. The researcher then fastens belt 120 on participant 60 as described in foregoing description. Belt 140 is fastened over the lower thighs of participant 60 as described in the foregoing description. Belt 150 is fastened over the participant's legs as described in the foregoing description. The researcher determines which foot is to be tested and then positions force-measuring device 102 on the selected foot such that sensor 104 physically contacts the top of the foot and the rear side of force-measuring device 102 faces the researcher. The researcher then wraps belt 160 over force-measuring device 102. In such a configuration, force-measuring device 102 is firmly positioned between the belt 160 and the participant's foot. Belt 170 is not used in this test. Participant 60 then flexes at the ankle to push the top of his foot up into sensor 104 while the researcher holds the force-measuring device 102 steady. Participant 60 continues to flex at the ankle until the force-measuring device 102 indicates that sufficient data has been obtained.

In order to test the participant's hip flexion muscles, participant 60 sits on top surface 18 of table section 12 so that the participant's legs extend over front edge 22 and the back of the participant's knees contact curved surface 28. The researcher fastens belt 120 on participant 60 as described in foregoing description. Belt 150 is fastened over the participant's legs as described in the foregoing description. Belts 160 and 170 are not used in this test. The researcher determines which of the participant's legs is to be tested. The researcher then positions force-measuring device 102 on the lower thigh of the leg to be tested such that sensor 104 physically contacts the lower thigh and the rear side of force-measuring device 102 faces the researcher. The researcher then wraps belt 140 over force-measuring device 102 and the participant's other thigh. In such a configuration, force-measuring device 102 is firmly positioned between the belt 140 and the participant's lower thigh of the leg to be tested. Participant 60 then attempts to lift the thigh of the leg to be tested with as much force as possible while the researcher holds the force-measuring device 102 steady. Participant 60 continues to lift the thigh until force-measuring device 102 indicates that sufficient data has been obtained.

In order to test the participant's knee extension muscles, participant 60 sits on top surface 18 of table section 12 so that the participant's legs extend over front edge 22 and the back of the participant's knees contact curved surface 28. The researcher fastens belt 120 on participant 60 as described in foregoing description. The researcher then fastens belt 140 over the participant's upper thighs. Belts 160 and 170 are not used in this test. The researcher then positions force-measuring device 102 on the shin of the participant's leg to be tested such that sensor 104 physically contacts the shin and the rear side of force-measuring device 102 faces the researcher. Optionally, a shin guard may be first placed on the shin and then force-measuring device 102 placed on the shin guard. The researcher then wraps belt 150 over force-measuring device 102 and the shin on the participant's other leg such that force-measuring device 102 is firmly positioned between the belt 150 and the shin of the participant's leg to be tested. Participant 60 then attempts to push his lower leg being tested forward in a kicking motion with as much force as possible while the researcher holds force-measuring device 102 steady. Participant 60 continues to push the lower leg forward until force-measuring device 102 indicates that sufficient data has been obtained.

In order to test the participant's knee flexion muscles, participant 60 sits on top surface 18 of table section 12 so that the participant's legs extend over front edge 22 and the back of the participant's knees contact curved surface 28. For this test, participant 60 is seated either fully to the right side or fully to the left side of table section 12 so that the leg to be tested is aligned with either front leg member 16A or 16B. The researcher fastens belt 120 on the participant as described in foregoing description. The researcher then fastens belt 140 over the participant's upper thighs. Belts 150, 160 and 170 are not used in this test. The researcher then positions force-measuring device 102 either on front leg member 16A or front leg member 16B of table section 12, depending upon which of the front leg members 16A or 16B corresponds to the participant's leg to be tested. Specifically, the researcher positions force-measuring device 102 on the selected front leg member such that the rear side of force-measuring device 102 abuts the selected front leg member and sensor 104 faces outward. Participant 60 then presses the calf of the leg being tested against sensor 104 with as much force as possible while the researcher holds the force-measuring device 102 steady. Participant 60 continues to press the calf backwards until force-measuring device 102 indicates that sufficient data has been obtained.

In order to test the participant's hip abduction muscles, participant 60 positions himself or herself on table section 12 so that his or her legs and thighs extend through open area 58 in frame section 34. The researcher secures belt 120 on participant 60 as described in the foregoing description. The researcher secures belt 170 on participant 60 and then positions force-measuring device 102 between the outside of the participant's knee to be tested and either support member 68 or 74, depending on which of the participant's legs is to be tested. For example, if the participant's right leg is to be tested, then the researcher positions force-measuring device 102 between support member 68 and the outside of the participant's right knee wherein the rear side of force-measuring device 102 abuts support member 68 and sensor 104 contacts the outside of the participant's right knee. Participant 60 then moves the knee to be tested laterally against sensor 104 with as much force as possible while the researcher holds force-measuring device 102 steady. Participant 60 continues this movement until force-measuring device 102 indicates that sufficient data has been obtained. In this test, belts 140, 150, 160 and 170 are not used. In some embodiments, a holder or cradle device (not shown) holds or secures force-measuring device 102 and is positioned on table section 12 so that it abuts support member 68.

In order to test the participant's hip adduction muscles, participant 60 positions himself or herself on table section 12 so that his or legs and thighs extend through open area 58 of frame section 34. The researcher secures belt 120 on the participant as described in the foregoing description. Belts 140, 150, 160 and 170 are not used. In order to facilitate understanding of this test, it is assumed that the participant's right leg is the leg to be tested. The researcher places force-measuring device 102 on the inside of the participant's knee to be tested such that sensor 104 physically contacts the participant's inner knee. The research then uses a smaller belt (not shown), such as Velcro® strap, and loops it through gap or space 69 between support member 68 and bracket 66 (see FIG. 5) and then around force-measuring device 102 and the participant's knee to be tested. Participant 60 then moves the knee to be tested medially and inward with as much force as possible while the researcher holds the force-measuring device 102 steady. Participant 60 continues this movement until force-measuring device 102 indicates that sufficient data has been obtained.

Apparatus 10 also allows other isometric muscle-strength measurements to be taken on a participant by positioning force-measurement device 102 at different locations on table section 12 or frame section 34. In such embodiments, cradle 100 is removably attached to different positions on table section 12 or frame section 34 in order to support the force-measuring device 102 while measuring isometric muscle strength of muscle groups in other parts of the participant's body. For example, force-measuring device 102 may be positioned at particular locations on table section 12 or frame section 34 in order to take shoulder measurements of participant 60 while he is seated on table section 12. Such shoulder measurements include shoulder flexion/extension, shoulder abduction, and shoulder internal/external rotation.

In some embodiments, ruler markings or other indicia may be applied to or formed on front leg members 16A and 16B and/or tracks 62 and 64 and/or vertical support member 44 in order to improve consistent positioning of participant 60 and force-measuring device 102.

In some embodiments, apparatus 10 includes a telescoping table extension with additional legs that will store under table section 12. This telescoping table extension allows a participant to be positioned in the prone position on table section 12 so that the participant can lay flat on his back. In such an embodiment, the telescoping table extension extends from rear edge 24 of table section 12. The telescoping table extension provides further functionality to apparatus 10 and allows additional muscle tests such as (i) prone hip flexion/extension and abduction/adduction, (ii) prone ankle dorsiflexion/plantar flexion and abduction/adduction, and (iii) prone shoulder flexion/extension and abduction/adduction and internal/external rotation.

Any suitable material may be used to fabricate apparatus 10. For example, table section 12 and frame section 34 may be fabricated from metals such as aluminum, steel or stainless steel, iron, copper, brass, etc. Any suitable fastening technique may be used to attach the sections of table section 12 and frame section 34 together, e.g. screws, bolts, rivets, welding, brazing, etc. Cradle 100 maybe fabricated from suitable materials such as plastics, resins, rubber, composite materials and metal. In an exemplary embodiment, cradle 100 is fabricated from plastic using a suitable 3-D printing technique.

The present invention provides many advantages and benefits. Specifically, apparatus 10 can be used with participants of various body sizes. Muscle groups to be tested are isolated with no discomfort to the participant. Apparatus 10 is easily portable and in some embodiments, frame section 34 is detachable from table section 12, lateral support members 26 are detachable and leg members 16A-D are pivotably attached to table section 12 so the leg members can be folded up for easy storage. Apparatus 10 is easily and quickly deployed on any solid, generally level surface and has a footprint of about 1 m². Force-measuring device 102 requires electrical power via one or more batteries but the remaining components of apparatus 10 do not require electrical power to operate. The researcher can easily secure participant 60 on table section 12 with belts or straps for purposes of isolating a muscle group of interest. Force-measuring device 102 can be positioned at several locations on apparatus 10 in order to accurately record the force exerted by participant 60. Because of the unique structure of apparatus 10, the researcher or clinician is not required to have greater strength than participant 60 in order to record measurements effectively and consistently. Any force that the researcher applies to the rear side of force-measuring device 102 for the purposes of stabilization of the force-measuring device 102 is significantly less than the force being applied by participant 60. The present invention allows for reliable and consistent maximal muscle strength measurements to be recorded by multiple researchers thereby increasing researcher scheduling flexibility. The present invention does not require researchers or clinician to have extensive experience using a force-measuring device (e.g. HHD) in order to effectively and consistently use such devices. The present invention also allows the same researcher to perform an increased number of strength assessments by removing much of the physical load that is typically required for use of force-measuring devices such as the HHD.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. An apparatus for measuring the isometric muscle strength of muscle groups of a participant, comprising:
   a table section having a top surface and a plurality of legs that support the top surface, the top surface having a front edge and a rear edge and being adapted to allow the participant to sit thereon;
   a generally upright frame section adjustably attached to the table section and spanning the top surface of the table section, the frame section being configured for bi-directional movement over the top surface of the table section such that the frame section is movable toward the front edge or toward the rear edge, the frame section having an open area above the top surface of the table section that is sized to allow a participant's legs and thighs to extend therethrough while the participant is seated on the top surface;
   at least one movement-impeding device adjustably attached to the frame section and configurable to a first state to prevent movement of the frame section and to a second state that allows movement of the frame section;
   a cradle movably attached to the generally upright frame section and configured to receive a force-measuring device, the cradle having a front opening and being vertically movable upward or downward; and
   a plurality of restraining devices attached to the table section and configured to be secured to various parts of the participant's body to stabilize the participant on the top surface of the table section and to isolate muscle groups that are to be tested.

2. The apparatus according to claim 1 further comprising a force-measuring device secured within the cradle, the force-measuring device having a sensor that protrudes from the front opening of the cradle so that it can be acted upon by a participant's torso when the participant is sitting on the top surface of the table section.

3. The apparatus according to claim 2 wherein the force-measuring device is a dynamometer.

4. An apparatus for measuring the isometric muscle strength of various muscle groups of a participant, comprising:
   a table section having a top surface and a plurality of legs that support the top surface, the top surface having a front edge and a rear edge and being adapted to allow a participant to sit thereon;

a generally upright frame section adjustably attached to the table section and spanning the top surface of the table section, the frame section being configured for bi-directional movement over the top surface of the table section such that the frame section is movable toward the front edge or toward the rear edge, the frame section having an open area above the top surface of the table section that is sized to allow a participant's legs and thighs to extend therethrough while the participant is seated on the top surface;

at least one movement-impeding device adjustably attached to the frame section and configurable to a first state to prevent movement of the frame section and to a second state that allows movement of the frame section;

a force-measuring device positioned on the frame section at a predetermined location so that it is acted upon by a participant's torso; and a plurality of restraining devices attached to the table section and configured to be secured to various parts of the participant's body to stabilize the participant on the top surface of the table section and to isolate muscle groups that are to be tested.

5. The apparatus according to claim 4 wherein the top surface of the table section is substantially horizontal and the generally upright frame section is substantially perpendicular to the top surface of the table section.

6. The apparatus according to claim 4 wherein the generally upright frame section is slidably attached to the table section.

7. The apparatus according to claim 4 wherein the table section has a first lengthwise end on one side of the table section and a second lengthwise end on an opposite side of the table section, and wherein the table section further comprises a first track attached to the first lengthwise end and a second track attached to the second lengthwise end, the generally upright frame section being slidably attached to the first track and the second track.

8. The apparatus according to claim 7 wherein the first track and second track extend beyond the rear edge of the top surface.

9. The apparatus according to claim 7 wherein the at least one movement-impeding device comprises a first movement-impeding device in proximity to the first track and a second movement-impeding device in proximity to the second track, wherein the first movement-impeding device and the second movement-impeding device are configurable to a first state to engage the first track and the second track, respectively, so as to prevent movement of the frame section and wherein the first movement-impeding device and second movement-impeding device are configurable to a second state to disengage the first track and the second track, respectively, so as to allow movement of the frame section.

10. The apparatus according to claim 4 further comprising a holder attached to the frame section, the force-measuring device being secured within the holder.

11. The apparatus according to claim 10 wherein the frame section includes a generally vertical frame member and the holder is adjustably attached to the frame member such that the holder is vertically movable upward or downward.

12. The apparatus according to claim 4 wherein the force-measuring device comprises a dynamometer.

13. The apparatus according to claim 4 wherein the plurality of restraining devices comprises a belt that is attached to the table section and which is adapted to secure the participant to the top surface of the table section.

14. The apparatus according to claim 4 wherein the plurality of restraining devices comprises a belt that is attached to the table section and adapted to secure the participant's thighs.

15. The apparatus according to claim 4 wherein the plurality of restraining devices comprises a belt that is attached to the table section and adapted to secure the participant's legs.

16. The apparatus according to claim 15 wherein the plurality of leg members of the table section includes a pair of front leg members and a pair of rear leg members, and wherein the belt is attached to the pair of front leg members and is adapted to secure the participant's legs when the participant's legs hang over the front edge of the top surface.

17. The apparatus according to claim 4 wherein the plurality of leg members of the table section includes a pair of front leg members and a pair of rear leg members and wherein the table section further comprises a plurality of lateral support members, wherein each lateral support member is attached to a pair of leg members and wherein one of the lateral support members is attached to the pair of front pair of leg members.

18. The apparatus according to claim 17 wherein the plurality of restraining devices comprises a belt that is attached to the lateral support member that is attached to the front pair of leg members and is adapted to secure at least one of the participant's ankles.

19. The apparatus according to claim 4 wherein the plurality of restraining devices comprises a belt that is attached to the table section and adapted to secure at least one of the participant's ankles.

20. An apparatus for measuring the isometric muscle strength of various muscle groups of a participant, comprising:

a table section having a top surface and a plurality of legs that support the top surface, the top surface having a front edge and a rear edge and being adapted to allow a participant to sit thereon, the table section having a first lengthwise end on one side of the table section and a second lengthwise end on an opposite side of the table section, the table section further comprising a first track attached to first lengthwise end and a second track attached to the second lengthwise end;

a generally upright frame section slidably attached to the first track and second track and spanning the top surface of the table section, the frame section being configured for bi-directional movement over the top surface of the table section such that the frame section is slidable toward the front edge and toward the rear edge, the frame section having an open area above the top surface of the table section that is sized to allow a participant's legs and thighs to extend therethrough while the participant is seated on the top surface;

a plurality of movement-impeding devices adjustably attached to the frame section and configurable to engage the first and second tracks to prevent movement of the frame section and configurable to disengage the first and second tracks to allow movement of the frame section;

a cradle movably attached to the generally upright frame section and configured to receive a force-measuring device, the cradle having a front opening and being vertically movable upward and downward;

a force-measuring device secured within the cradle, the force-measuring device having a sensor that protrudes from the front opening of the cradle so that it can be acted upon by a participant's torso when the participant is sitting on the top surface of the table section; and a plurality of belts attached to various portions of the table section and configured to be secured to various parts of the participant's body to stabilize the participant on the top surface of the table section and to isolate muscle groups that are to be tested.

\* \* \* \* \*